US00PP08177P

United States Patent [19]

Corrin

[11] Patent Number: Plant 8,177

[45] Date of Patent: Mar. 16, 1993

[54] "RUBY" APRICOT TREE

[76] Inventor: Allen A. Corrin, 6541 S. Holbrook, Reedley, Calif. 93654

[21] Appl. No.: 897,444

[22] Filed: Jun. 5, 1992

Related U.S. Application Data

[63] Continuation of Ser. No. 581,632, Sep. 10, 1990.

[51] Int. Cl.[5] ..... A01H 5/00

[52] U.S. Cl. ..... Plt./39

[58] Field of Search ..... Plt./39

[56] References Cited

U.S. PATENT DOCUMENTS

P.P. 1,732 7/1958 Culbashian ..... Plt. 39

*Primary Examiner*—James R. Feyrer

*Attorney, Agent, or Firm*—Worrel & Worrel

[57] ABSTRACT

A new and distinct variety of apricot tree which is somewhat remotely similar to the Castlebrite apricot tree (unpatented), but from which it is distinguished therefrom by producing fruit which are mature for harvesting and shipment approximately two weeks later than the fruit produced by the Castlebrite apricot tree and which further produces a high quality, fresh market apricot of medium size and possessing an unusually high degree of red skin coloration in a distinctive striped pattern and has a substantially richer flavor and possesses better balance.

1 Drawing Sheet

This is a continuation of copending application Ser. No. 07/581,632 filed on Sep. 10, 1990.

BACKGROUND OF THE NEW VARIETY

The present invention relates to a new and distinct variety of apricot tree, which will hereinafter be denominated varietally as "Ruby", and more particularly to a apricot tree which produces fruit which are mature for commercial harvesting and shipment approximately June 9 to June 12 in the San Joaquin Valley of central California, and which further is distinguished as to novelty by producing a freestone fruit, which has a flavor superior to that of existent commercial varieties and which has a coloration having a high percentage of red present with a blush coloration occurring in a distinctive striped pattern.

There are a number of criteria within which a commercial variety of tree fruit must excel if it is to be a success in the fresh market. Among these are ripening date, flavor, texture, shipping quality and the like. Another criterion is the coloration of the skin of the fruit. Typically, fruit having high coloration is commercially desirable in that it is attractive and therefore appealing to the purchaser. More subtly, high coloration, particularly if different from that of competing commercial varieties, attracts immediate attention in the marketplace which substantially enhances the likelihood of commercial success.

Fresh market apricot varieties are characterized as to coloration typically by yellow to orange skin coloration in some instances having a slight red blush. The uniformity of this coloration among commercial varieties means that visibly there is little to distinguish the varieties from each other. Accordingly, particularly in apricot varieties of tree fruit it is highly desirable to develop a variety which produces fruit which not only has superior characteristics as to flavor, texture, ripening date and shipping quality, but importantly has a skin of high coloration and distinctive appearance.

ORIGIN AND ASEXUAL REPRODUCTION OF THE NEW VARIETY

The present variety of apricot tree hereof was discovered by the inventor in his orchard, which is located at 10442 S. East Avenue, Reedley, Calif. 93654 in 1987.

The variety was discovered as a sport of the Royal apricot tree (unpatented). The sport was discovered in a one-half (½) acre experimental plot which contained many known varieties of fruit trees, which was part of a seven acre parcel and which the inventor had purchased. The inventor conferred with the previous owner of the property and determined that the previous owner was unaware of the distinctive characteristics of the sport.

The new variety was asexually reproduced by grafting on the same property by the inventor in 1988 and the distinctive characteristics confirmed to have identically reproduced themselves in the asexually reproduced trees in June, 1990.

SUMMARY OF THE NEW VARIETY

The "Ruby" apricot tree is characterized as to novelty by producing a freestone fruit which has a red skin coloration in a distinctive striped pattern. The fruit produced by the "Ruby" apricot tree is ripe for commercial harvesting and shipment approximately June 9 to June 12 in the San Joaquin Valley of central California. The new and novel variety is perhaps most closely similar to the Castlebrite apricot tree (unpatented), but which is distinguishable therefrom and is characterized as a high quality, fresh market apricot of medium size, ripening in the second week of June and possessing an unusually high degree of red skin coloration in a distinctive striped pattern.

In comparison with the fruit of the Castlebrite apricot tree, the new variety is slightly over two weeks later in maturity with harvest beginning on June 9 in 1989. In contrast, the Castlebrite apricot tree is usually harvested approximately in the third or last week of May in the central valley of California. The new variety is equal to, or slightly larger than, the Castlebrite in size, but is substantially superior to the Castlebrite in flavor.

The Castlebrite is generally regarded as only of fair quality with weak flavor and high acidity. The new variety has substantially richer flavor and possesses better balance.

The exterior appearance of the new variety and Castlebrite vary substantially. The Castlebrite, like most apricot varieties grown in California, has mostly yellow to orange skin coloration with occasionally a slight amount, perhaps ten to twenty percent (10% to 20%), red blush present on fruit exposed to direct sunlight. In comparison, the new variety has a much greater percentage of the fruit area covered with red, that is from sixty to ninety percent (60% to 90%). In addition, the blush coloration of the new variety occurs in a distinctive striped pattern not commonly found in apricots, rather than in a washed or block pattern as is more common with other apricot varieties.

BRIEF DESCRIPTION OF THE DRAWING

The accompanying drawing is a color photograph of mature fruit of the new variety showing one in top plan view, a second in side elevation showing the suture, a third in side elevation showing the side thereof approximately 90 degrees from the suture, a fourth sectioned along the suture and laid open to expose the stone and, in the other half, the stone well and a fifth also shown in top plan view; three stones of the new variety, one positioned to show the ventral edge, a second positioned to show the dorsal edge and the third positioned to show the side thereof; portions of representative branches; and representative foliage.

DETAILED DESCRIPTION

Referring more specifically to the pomological details of this new and distinct variety of apricot tree, the following has been observed under the ecological conditions prevailing at the orchard of origin which is located at Reedley, Calif. All major color code designations are by reference to the *Dictionary of Color,* by Maerz and Paul, Second Edition, published in 1950.

TREE

Generally:

*Vigor.*—Vigorous and hardy.

*Chilling requirements.*—Grown under typical central San Joaquin Valley climatic conditions.

*Figure.*—Upright-spreading in form and open in density with eventual form determined by pruning.

*Productivity.*—Productive.

*Regularity of bearing.*—Regular.

Trunk:

*Size.*—Large in diameter.

*Surface texture.*—Moderately coarse. Bark finely furrowed and somewhat scaly.

*Color.*—Oldest bark — Dark charcoal (56-C-2). Less mature areas of the trunk more smooth and more charcoal-grey (56-E-2) in color.

*Lenticels — numbers.*—Numerous.

*Lenticels — size.*—Medium.

Branches:

*Size.*—Medium (average).

*Surface texture.*—Relatively smooth.

*Color — one year or older wood.*—Chocolate brown (8-J-10).

*Color — immature branches.*—Green (20-K-5). Most exposed shoots tinged with red. Tips of new expanding shoots also strongly tinged with red coloration. The color of the branches of the variety of apricot tree of U.S. Plant Pat. No. 1,732 is Moro Red #7-L-10 to 8-C-11.

Surface texture — immature growth.—Smooth.

LEAVES

Size:

*Generally.*—Measurements taken from large leaves growing near midpoint of current season's shoot.

*Average length.*—103 mm (4.12 inches) which include the leaf petiole. The length of the leaves of the variety of apricot tree of U.S. Plant Pat. No. 1,732 is 2⅞ inches.

*Average width.*—79 mm (3.16 inches). The width of the leaves of the vareity of apricot tree of U.S. Plant Pat. No. 1,732 is 3⅛ inches.

*Thickness.*—Average.

Form:

Broadly cordate. Leaf tip acuminate and most often slightly twisted.

Color:

*In young leaves.*—Upwardly disposed surface — Medium green (23-J-8) to somewhat lighter green (22-K-6). Downwardly disposed surface — Grey-green (21-K-5). As leaves mature, they taken on a distinctly darker coloration, with upper leaf surfaces a dull dark green overlain with purple color tones (56-H-3). In the variety of apricot tree of U.S. Plant Pat. No. 1,732, the color of the tops of the leaves is 22 J-7 and the underside 22 L-3.

*Leaf vein.*—Mid-vein on lower leaf surface a light green (19-J-4). The mid-vein on the under side of mature leaves are colored purple (7-E-4), especially basally.

Marginal form:

*Generally.*—Coarsely serrate, at times doubly so, with largest serrations over the apical end of the leaf. Serrations become very broad and somewhat indistinct across the basal end of the leaf. In the variety of apricot tree of U.S. Plant Pat. No. 1,732, the marginal form of the leaves is minutely serrate.

Leaf margin: Moderately undulate.

Glandular characteristics: Medium in size, most often globose in form. Gland location and number can vary substantially. Most often one to three glands are present, located alternately on the petiole 4 mm (0.16 inches) to 7 mm (0.28 inches) below the basal edge of the leaf margin. At times no gland is present or, at other times, up to five can appear. At times, one to three glands can also be present on the basal edge of the leaf margin. These can occur on the margin itself or the glands can be present on stalks attached to the margin. Glands are shiny and reddish-brown (7L-9) in color initially, but darken and deteriorate somewhat with age.

Petiole:

*Length.*—Moderately long averaging 18 mm. (0.72 inches) to 25 mm (1 inch). In the variety of apricot tree of U.S. Plant Pat. No. 1,732, the petiole length is 1 inch.

*Thickness.*—Average 1.5 mm (0.06 inches) to 2.0 mm (0.08 inches).

*Color.*—Medium violet (7-C-4).

Stipules: Most often, two rather small stipules present at first, subtending the leaf petiole.

*Length.*—3 mm (0.12 inches) to 4 mm (0.16 inches).

*Color.*—Pale green (18-G-3). Many stipules are early deciduous, but a small percentage remain attached on mature leaves.

FLOWERS

Flower buds:

*Size.*—Medium.

*Form.*—Conic.

*Surface texture.*—Scales covered with a fine grey pubescence.

Flower bud scales:

*Color.*—Dark chestnut brown (8-J-10).

Flower:

*Size.*—Generally — Medium to slightly below average.

*Diameter.*—Fully expanded bloom averages 14 mm (0.56 inches) to 17 mm (0.68 inches).

Date of bloom: Medium to slightly late in relation to other commercial apricot varieties reaching full bloom on Mar. 2, 1990.

Size:

*Generally.*—Medium to slightly below average in size.

Bloom quantity: Abundant and well distributed throughout tree. Normally 2 to 3 flower buds present per node, most commonly 2.

Petals:

*Size.*—Generally — Medium to slightly below average.

*Form.*—Variable, from globose to slightly oval.

*Length.*—Average 7 mm (0.28 inches) to 8 mm (0.32 inches).

*Width.*—Average 6 mm (0.24 inches) to 7 mm (0.28 inches).

*Color.*—Reddish pink (3-J-3) when young, darkening to a purple-pink (4-G-2) with age. Veination also becomes more prominent with age, darkening to a purple (4-I-4) coloration. In the variety of apricot tree of U.S. Plant Pat. No. 1,732, the flower coloration is "pinkish".

Petal claws:

*Form.*—Truncate, small in size and somewhat narrow.

*Color.*—Dark red-pink (3-F-4).

Petal margin: Slightly undulate.

Petal apex: Variable in form, but most often rounded.

Pedicel:

*Size.*—Relatively short. Average 2.0 mm (0.08 inches) in length and 1.5 mm (0.06 inches) in thickness.

*Color.*—Light green (19-G-2).

Nectaries:

*Color.*—Orange (12-L-10) basally with purple (6-I-3) coloration over the upper portion. Colors dull with age.

Anthers: Medium in size, light yellow (10-I-2) in color.

Pollen: Abundant with yellow (10-K-2) coloration.

Stamens:

Size.—Length 8 mm (0.32 inches) to 10 mm (0.40 inches) at full maturity and slightly longer than pistil at full extension.

*Color.*—Light pink-rose (2-G-1) when young becoming a darker rose (4-H-2) with age.

Pistil:

*Size.*—Length average 8 mm (0.32 inches) to 9 mm (0.36 inches) including ovary.

*Color.*—Very light green (17-J-2).

FRUIT

Maturity when described: Ripe for commercial harvesting and shipment approximately June 9 to June 12 at Reedley, Calif. The date of maturity of the fruit of the variety of apricot tree of U.S. Plant Pat. No. 1,732 is the last week of June.

Size:

*Generally.*—Uniform, medium size.

Average diameter in the axial plane.—50 mm (2 inches). The fruit of the variety of apricot tree of U.S. Plant Pat. No. 1,732 is 1⅝ inchesin diameter in the axial plane.

*Average diameter in cheek plane.*—48 mm (1.92 inches).

*Average diameter in the suture plane.*—52 mm (2.08 inches). The fruit of the variety of apricot tree of U.S. Plant Pat. No. 1,732 is 1-9/16 inches in diameter in the suture plane.

Form:

*Uniformity.*—Uniform.

*Symmetry.*—Slightly asymmetrical with one-half slightly larger than the other. Nearly oval in axial aspect with some lateral compression. Generally globose in lateral aspect.

Suture:

*Generally.*—A very distinct suture line present from base to apex, 1.5 (0.06 inches) to 2.0 mm (0.08 inches) in width. Suture color a dark violet (56-J-9). Suture crease deeper at basal end of fruit, within the stem cavity.

Ventral surface:

*Generally.*—Distinctly lipped on most fruit. Lipping can occur equally on both sides or be slightly stronger on one side.

Stem cavity:

*Generally.*—Small in size.

*Width.*—Average range from 14 mm (0.56 inches) to 18 mm (0.72 inches).

*Depth.*—Shallow in depth — 3 mm (0.12 inches) to 5 mm (0.2 inches). The stem cavity of the fruit of the vareity of apricot tree of U.S. Plant Pat. No. 1,732 is 3/16 inch in depth.

*Shape.*—Round to slightly oval in form.

Stem:

*Generally.*—Medium — 4 mm (0.16 inches) to 5 mm (0.2 inches) in length; 3 mm (0.12 inches) to 3.5 mm (0.14 inches) in thickness.

*Color.*—Green-brown (14-K-4).

Apex:

*Shape.*—Rounded. Very slightly depressed at pistil point.

Pistil point:

*Position.*—Apical.

Base:

*Generally.*—Slightly truncate. Base very oblique to fruit axis, shorter on dorsal suture side.

Skin:

*Thickness.*—Average.

*Tendency to crack.*—No observed tendency to crack.

*Pubescence.*—Scant, short pubescence present.

*Blush color.*—Medium red (6-K-10) to slightly darker red (6-L-10) with at times some purplish tones. Blush occurs over 60 to 90 percent of fruit surface in a mottled and striped pattern with striping especially noticeable over the basal shoulders of the fruit.

*Ground color.*—Yellow-cream (11-K-5) contrasting with the blush coloration. The skin coloration of the fruit of the variety of apricot tree of U.S. Plant Pat. No. 1,732 is 7-J-1 to 7-J-3.

*Flesh color.*—At commercial maturity — Uniform orange (11-J-10) from skin to pit cavity. The coloration of the flesh of the fruit of the variety of apricot tree of U.S. Plant Pat. No. 1,732 is 9-L-8.

*Flavor.*—Good, rich, well balanced.

*Aroma.*—Moderate, pleasant.

*Texture.*—Firm at commercial maturity, softening with advancing maturity.

*Fibers — numbers.*—Medium in number, moderately long.

*Fibers — texture.*—Relatively tender.

*Ripening.*—Ripens evenly.

*Eating quality.*—Very good, well above average.

Stone:

*Attachment.*—Freestone. Some very light attachment of fibers along the ventral suture area.

*Fibers — numbers.*—Few.

*Fibers — length.*—Moderately short.

*Size.*—Generally — Medium. Length — 25 mm (1 inch) to 28 mm (1.12 inches). Width — 24 mm (0.96 inches) to 28 mm (1.12 inches). Thickness — 13 mm (0.52 inches) to 14 mm (0.56 inches).

*Form.*—Generally — Slightly irregular but most often globose.

*Apex.*—Shape — Very smooth and rounded with no apical tip.

*Color.*—Dry — Tan-brown (12-K-6) to a slightly darker brown (13-J-8).

*Base.*—Shape — Generally rounded.

*Sides.*—Generally — Relatively smooth with a slightly pebbled surface. Stone sides nearly equal to only slightly unequal.

*Hilum.*—Average to slightly larger than average. Generally a narrow oval in form with the edge of hilum which borders the ventral suture substantially eroded.

*Ridges.*—Two slightly raised ridges, one on each side of the edge run, from the base to the apex. These are roughly parallel to, but 5 mm (0.2 inches) to 6 mm (0.24 inches) below, the ventral edge and converge with the ventral edge both basally and apically. Numerous (6 to 10) small oval pits are usually present along and on both sides of the ventral suture area.

*Dorsal edge.*—Rounded in shape with a deep and moderately wide groove present apically and basally but not present in the area of mid-stone along the dorsal edge. The mid area of the dorsal edge is quite smooth, with the exception of the presence of several (3 to 5) relatively large oval pits along the edge.

*Ventral edge.*—Medium thickness with a narrow, at times slightly raised wing present from the base nearly, but not entirely, reaching to the apex.

*Tendency to split.*—None observed.

Use: Fresh market apricot for use in local markets as well as for long distance shipping.

Keeping quality: Good.

Although the new variety of apricot tree possesses the described characteristics noted above as a result of the growing conditions prevailing at Reedley, Calif. in the San Joaquin Valley of central California, it is to be understood that variations of the usual magnitude and characteristics incident to changes in growing conditions, fertilization, pruning and pest control are to be expected.

Having thus described and illustrated my new variety of nectarine tree, what I claim as new and desire to be secured by Plant Letters Patent is:

1. A new and distinct variety of apricot tree substantially as illustrated and described and which is a sport of the "Royal" apricot tree (unpatented) and is somewhat remotely similar to the "Castlebrite" apricot tree (unpatented), but which is distinguished therefrom and characterized principally as to novelty by producing fruit which are mature for commercial harvesting and shipment approximately June 9 to June 12 in the San Joaquin Valley of central California, which has superior flavor and which has a skin coloration having a much higher percentage of the surface area covered with a red coloration and a blush coloration occurring in a striped pattern.

* * * * *

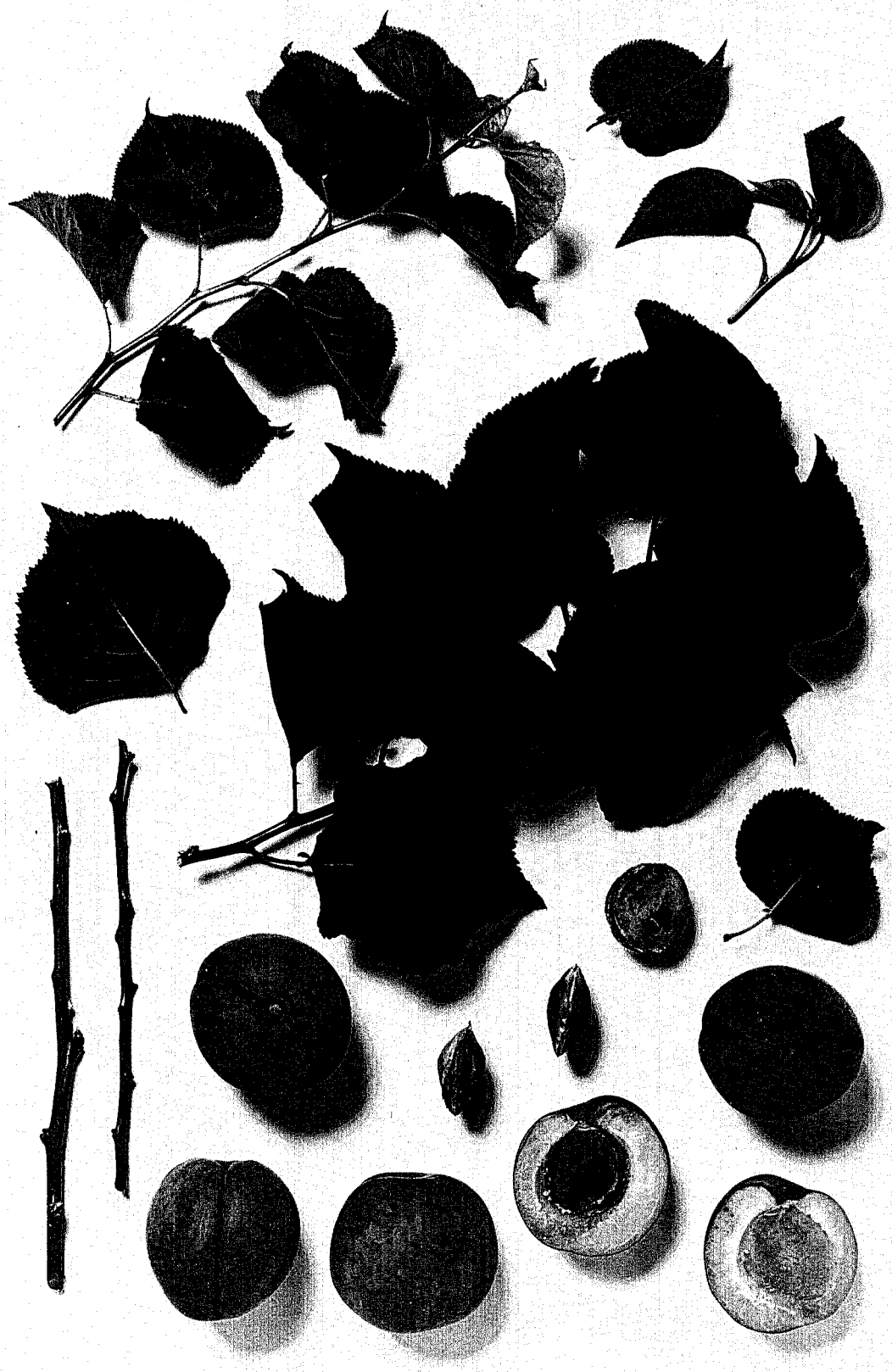

UNITED STATES PATENT AND TRADEMARK OFFICE

CERTIFICATE OF CORRECTION

PATENT NO. : Plant 8,177

DATED : March 16, 1993

INVENTOR(S) : ALLAN A. CORRIN

It is certified that error appears in the above-identified patent and that said Letters Patent is hereby corrected as shown below:

TITLE PAGE:
Inventor, delete "Allen" and substitute ---Allan---.

Column 4, line 11-12, delete "include" and substitute ---includes---.

Column 4, line 27, delete "taken" and substitute ---take---.

Column 6, line 12, insert a space between "inches" and "in".

Column 7, line 20, delete "light" and substitute ---slight---.

Signed and Sealed this

Twenty-third Day of November, 1993

*Attest:*

Bruce Lehman

BRUCE LEHMAN

*Attesting Officer*

*Commissioner of Patents and Trademarks*